(12) United States Patent
Tanabe et al.

(10) Patent No.: US 9,423,349 B2
(45) Date of Patent: Aug. 23, 2016

(54) OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

(71) Applicant: OLYMPUS CORPORATION, Tokyo (JP)

(72) Inventors: Tetsuya Tanabe, Tokyo (JP); Mitsushiro Yamaguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 145 days.

(21) Appl. No.: 14/178,442

(22) Filed: Feb. 12, 2014

(65) Prior Publication Data

US 2014/0162268 A1   Jun. 12, 2014

Related U.S. Application Data

(63) Continuation of application No. PCT/JP2012/067692, filed on Jul. 11, 2012.

(30) Foreign Application Priority Data

Aug. 15, 2011   (JP) .................................. 2011-177453

(51) Int. Cl.
*G01N 21/64*   (2006.01)
*G01N 21/51*   (2006.01)
(Continued)

(52) U.S. Cl.
CPC ................ *G01N 21/64* (2013.01); *G01N 15/14* (2013.01); *G01N 15/1429* (2013.01);
(Continued)

(58) Field of Classification Search
None
See application file for complete search history.

(56) References Cited

U.S. PATENT DOCUMENTS

| 4,251,733 A | 2/1981 | Hirleman, Jr. |
| 4,885,473 A | 12/1989 | Shofner et al. |

(Continued)

FOREIGN PATENT DOCUMENTS

| CN | 101946180 A | 1/2011 |
| EP | 1 906 172 A1 | 4/2008 |

(Continued)

OTHER PUBLICATIONS

Extended European Search Report dated Oct. 20, 2014, issued in related EP Application No. 12770835.2 (10 pages).

(Continued)

*Primary Examiner* — Kara E Geisel
*Assistant Examiner* — Amanda Merlino
(74) *Attorney, Agent, or Firm* — Westerman, Hattori, Daniels & Adrian, LLP

(57) ABSTRACT

In the scanning molecule counting method detecting light of a light-emitting particle in a sample solution using a confocal or multiphoton microscope, there is provided an optical analysis technique enabling the scanning in a sample solution with moving a light detection region in a broader area or along a longer route while making the possibility of detecting the same light-emitting particle as different particles as low as possible and remaining the size or shape of the light detection region unchanged as far as possible. In the inventive optical analysis technique, there are performed detecting light from the light detection region and generating time series light intensity data during moving the light detection region along the second route whose position is moved along the first route, and thereby, the signal indicating light from each light-emitting particle in a predetermined route is individually detected using the time series light intensity data.

27 Claims, 7 Drawing Sheets

Figure 1A:
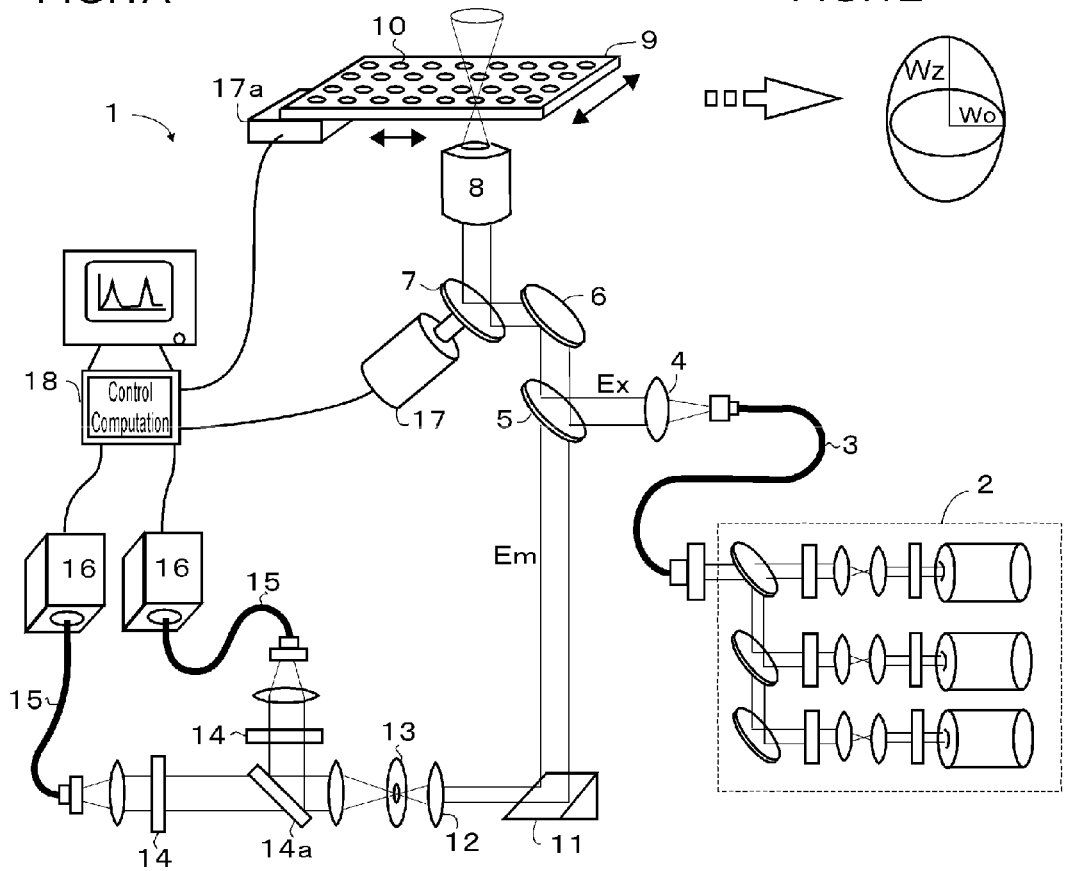

(51) Int. Cl.
*G01N 15/14* (2006.01)
*G02B 21/00* (2006.01)

(52) U.S. Cl.
CPC .......... *G01N 15/1434* (2013.01); *G01N 21/51* (2013.01); *G01N 21/645* (2013.01); *G01N 21/6408* (2013.01); *G01N 21/6452* (2013.01); *G01N 21/6458* (2013.01); *G01N 21/6486* (2013.01); *G02B 21/008* (2013.01); *G02B 21/0032* (2013.01); *G02B 21/0076* (2013.01); *G01N 2021/6419* (2013.01); *G01N 2021/6441* (2013.01); *G01N 2201/103* (2013.01); *G01N 2201/105* (2013.01)

(56) References Cited

U.S. PATENT DOCUMENTS

| | | | |
|---|---|---|---|
| 5,319,575 | A | 6/1994 | Lilienfeld |
| 5,866,336 | A | 2/1999 | Nazarenko et al. |
| 5,900,933 | A | 5/1999 | Schwartz et al. |
| 6,280,960 | B1 | 8/2001 | Carr |
| 6,376,843 | B1 | 4/2002 | Palo |
| 6,388,746 | B1 | 5/2002 | Eriksson et al. |
| 6,388,788 | B1 | 5/2002 | Harris et al. |
| 6,400,487 | B1 | 6/2002 | Harris et al. |
| 6,403,338 | B1 | 6/2002 | Knapp et al. |
| 6,449,042 | B1 | 9/2002 | Hamann |
| 6,710,871 | B1 | 3/2004 | Goix |
| 6,782,297 | B2 | 8/2004 | Tabor |
| 6,856,391 | B2 | 2/2005 | Garab et al. |
| 6,927,401 | B1 | 8/2005 | Palo |
| 8,284,484 | B2 | 10/2012 | Hoult et al. |
| 8,471,220 | B2* | 6/2013 | Yamaguchi ........ G01N 15/1456 250/458.1 |
| 8,541,759 | B2* | 9/2013 | Yamaguchi ........ G01N 15/1456 250/458.1 |
| 8,710,413 | B2* | 4/2014 | Yamaguchi ........ G01N 15/1456 250/203.3 |
| 9,068,944 | B2* | 6/2015 | Tanabe ................ G01N 21/6408 |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2003/0036855 | A1 | 2/2003 | Harris et al. |
| 2003/0218746 | A1 | 11/2003 | Sampas |
| 2004/0022684 | A1 | 2/2004 | Heinze et al. |
| 2004/0051051 | A1 | 3/2004 | Kato et al. |
| 2004/0150880 | A1 | 8/2004 | Nakata et al. |
| 2005/0260660 | A1 | 11/2005 | van Dongen et al. |
| 2006/0078998 | A1 | 4/2006 | Puskas et al. |
| 2006/0158721 | A1 | 7/2006 | Nakata et al. |
| 2006/0256338 | A1 | 11/2006 | Gratton et al. |
| 2008/0052009 | A1 | 2/2008 | Chiu et al. |
| 2008/0156999 | A1 | 7/2008 | Nishiwaki et al. |
| 2008/0158561 | A1 | 7/2008 | Vacca et al. |
| 2009/0159812 | A1 | 6/2009 | Livingston |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2010/0301231 | A1 | 12/2010 | Yamaguchi |
| 2011/0192595 | A1 | 8/2011 | Ronaes et al. |
| 2014/0099630 | A1 | 4/2014 | Nakata |
| 2014/0162268 | A1 | 6/2014 | Tanabe et al. |

FOREIGN PATENT DOCUMENTS

| | | |
|---|---|---|
| EP | 2 752 655 A | 7/2014 |
| EP | 2 840 380 A1 | 2/2015 |
| JP | 63-225145 A | 9/1988 |
| JP | 04-337446 A | 11/1992 |
| JP | 2002-507762 A | 3/2002 |
| JP | 2002-543414 A | 12/2002 |
| JP | 2004-506192 A | 2/2004 |
| JP | 2005-98876 A | 4/2005 |
| JP | 2005-099662 A | 4/2005 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-190730 A | 9/2010 |
| JP | 2011-02415 A | 1/2011 |
| JP | 2011-508219 A | 3/2011 |
| WO | 98/16814 A1 | 4/1998 |
| WO | 99/47963 A | 9/1999 |
| WO | 00/66985 A1 | 11/2000 |
| WO | 00/71991 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2012/014778 A1 | 2/2012 |
| WO | 2012/050011 A1 | 4/2012 |
| WO | 2012-144528 A1 | 10/2012 |
| WO | 2013-024650 A1 | 2/2013 |

OTHER PUBLICATIONS

Office Action dated Apr. 16, 2015, issued in related U.S. Appl. No. 13/946,091 (21 pages).
Office Action dated Apr. 24, 2015, issued in Chinese Patent Application No. 2012800041770.X, with English translation (27 pages).
Office Action dated Jun. 1, 2015, issued in Chinese Patent Application No. 201280005999.8, with English translation (15 pages).
Chinese Office Action dated Oct. 10, 2014, issued in corresponding Chinese Application No. 201280005999.8; w/English Translation. (20 pages).
Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, (p. 1612-1618)
U.S. Office Action dated Apr. 2, 2013, issued in related U.S. Appl. No. 13/596,280.
Kask, Peet et al., "Two-Dimensional Fluorescence Intensity Distribution Analysis: Theory and Applications", Biophysical Journal, Apr. 2000, vol. 78, (p. 1703-1713).
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483, Mar. 30, 2012.
Chinese Office Action dated Aug. 9, 2013, issued in related Chinese application No. 201180011640.7; w/ English Translation (16 pages).
International Search Report Mar. 29, 2011, issued in related PCT/JP2011/053482.
International Preliminary Report on Patentability (PCT/IPEA/409) issued in related PCT/JP2011/053482, Mar. 3, 2012.
U.S. Office Action dated Jan. 3, 2013, issued in related U.S. Appl. No. 13/597,825.
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481, Jun. 15, 2012.
Goodwin, Peter et al., "Rapid Sizing of Individual Fluorescently Stained DNA Fragments by Flow Cytometry," Nucleic Acids Research, 1993, vol. 21, No. 4 (p. 803-806).
Keller, Richard et al., "Single-Molecule Fluorescence Analysis in Solution," Applied Spectroscopy, 1996, vol. 50, No. 7, (p. 12A-32A).

(56) References Cited

OTHER PUBLICATIONS

Lee, Yuan-Hsiang et al., "Laser-Induced Fluorescence Detection of a Single Molecule in a Capillary," Analytical Chemistry, dated Dec. 1, 1994, vol. 66, No. 23, (p. 4142-4149).
Li, Haitao et al., "Ultrasensitive Coincidence Fluorescence Detection of Single DNA Molecules," Analytical Chemistry, dated Apr. 1, 2003, vol. 75, No. 7, (p. 1664-1670).
Nie, Shuming et al., "Probing Individual Molecules with Confocal Fluorescence Microscopy," Science, dated Nov. 11, 1994, vol. 266, (p. 1018-1021).
Tahari, Abdel. "Fluorescence Correlation Spectroscopy: Ultrasensitive Detection in Clear and Turbid Media," University of Illinois, 2006, (p. 1-88).
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, (p. 2157-2159).
Itoh et al., "A New Method for Detection of Influenza Viruses by Single Particle-Recognition Based on the Principle of Fluorescence Correlation Spectroscopy," Chemistry and Biology, 2009, vol. 47, No. 12, (p. 823-830).
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243.
Japanese Office Action dated Dec. 18, 2012 issued in related JP application No. 2012-503060; w/ English Translation (6 pages).
International Search Report dated Feb. 14, 2012, issued in related PCT/JP2012/051175.
International Search Report dated Aug. 28, 2012, issued in related PCT/JP2012/068947.
U.S. Office Action dated Feb. 6, 2014, issued in related U.S. Appl. No. 13/946,091.
U.S. Office Action dated May 13, 2014, issued in related U.S. Appl. No. 13/946,091.
International Search Report dated Nov. 29, 2011, issued in related PCT/JP2011/072939.
International Search Report dated Aug. 14, 2012, issued in related PCT/JP2012/067692.
Kinjo, Masataka, "Single molecule protein, nucleic acid, and enzyme assays and their procedures; Single molecule detection by fluorescence correlation spectroscopy", Protein, Nucleic Acid, Enzyme, 1999, vol. 44, No. 9, pp. 1431-1438, w/ English machine translation.
Almes-Meyer, F.J., "Nanoparticle Immunoassays: A new Method for Use in Molecular Diagnostics and High Throughput Pharmaceutical Screening based on Fluorescence Correlation Spectroscopy", edit. R. Rigler, Springer, Berlin, 2000, pp. 204-224.
Kato, Noriko et al., "A single molecule analyzer that enable new analysis of DNA and protein interactions", Genome Medical Business Project, 2002, vol. 6, No. 2, pp. 271-277.
Peet Kask et al., "Fluorescence-intensity distribution analysis and its application in biomolecular detection technology", PNAS, vol. 96, No. 24, Nov. 23, 1999, pp. 13756-13761.
International Search Report for PCT/JP2012/067692, Mailing Date of Aug. 14, 2012.
Extended European Search Report dated Mar. 31, 2015, issued in European Patent Application No. 12823870.6 (15 pages).
Extended European Search Report dated Apr. 10, 2015, issued in European Patent Application No. 12827023.8 (13 pages).
Office Action dated Mar. 25, 2015, issued in Chinese Patent Application No. 201280039905.9, with English translation (34 pages).
Advisory Action dated Feb. 2, 2016, issued in corresponding U.S. Appl. No. 13/946,091.
Chinese Office Action dated Jan. 25, 2016, issued in Chinese Application No. 201280005999.8.
Final Office Action dated Sep. 29, 2015, issued in corresponding U.S. Appl. No. 13/946,091 (23 pages).
Final Office Action dated Sep. 28, 2015, issued in corresponding U.S. Appl. No. 13/746,968 (24 pages).
International Search Report dated Mar. 15, 2016, issued in PCT/JP2015/084490.
Non-Final Office Action dated Jun. 24, 2016, issued in related U.S. Appl. No. 14/188,375. (9 pages).

* cited by examiner

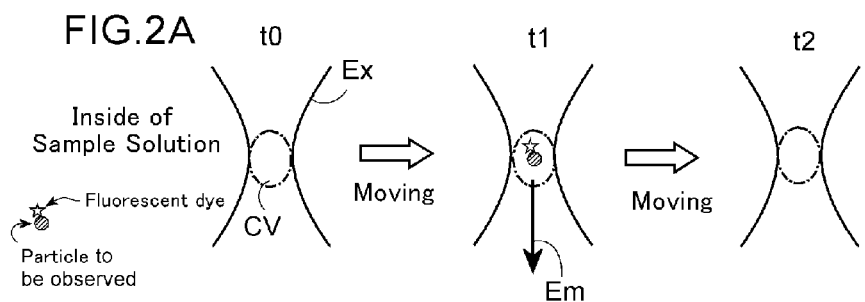
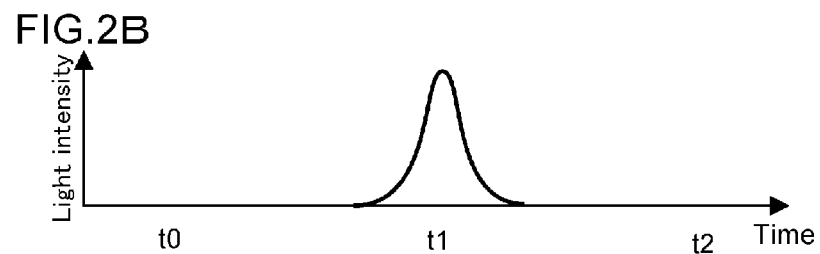
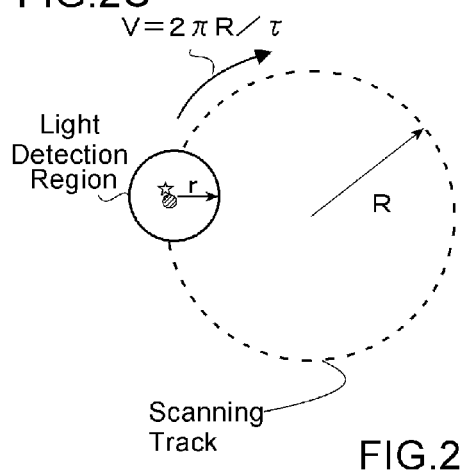
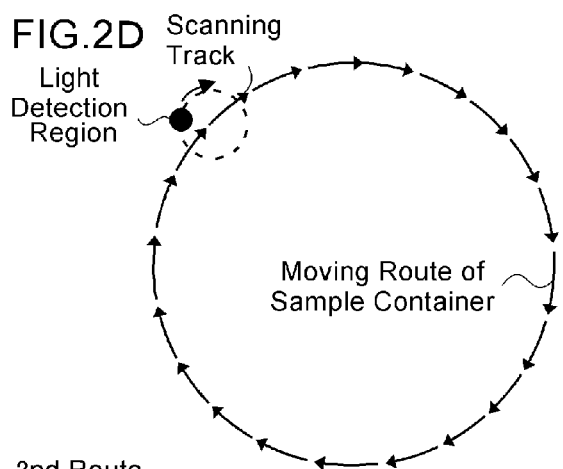
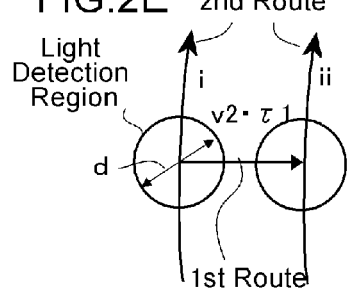

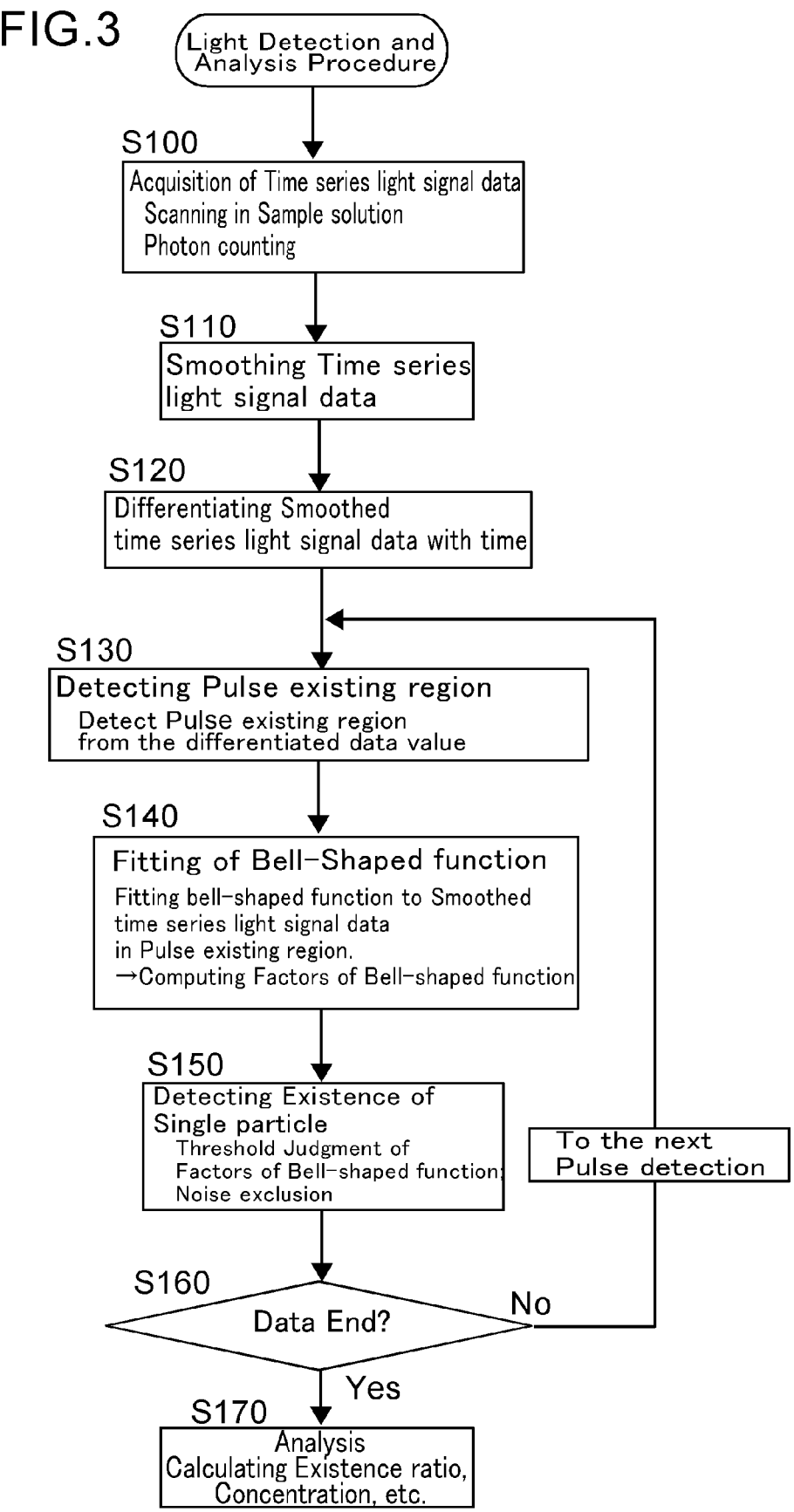

FIG.4A
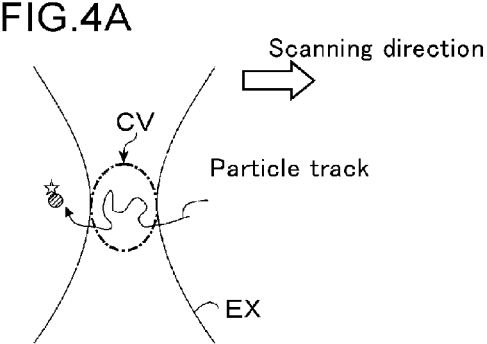
FIG.4B
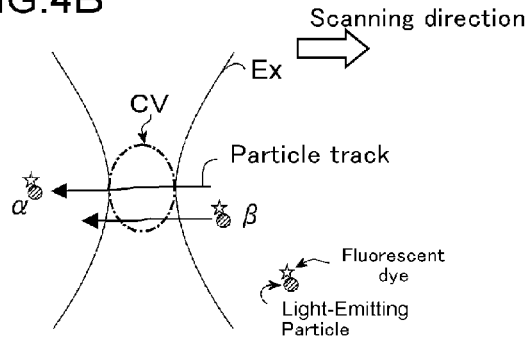
FIG.4C
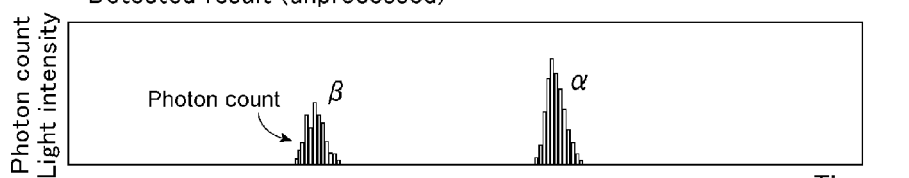
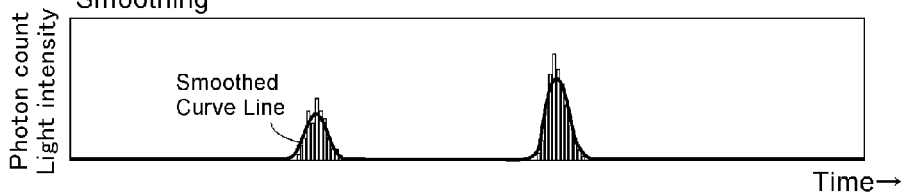
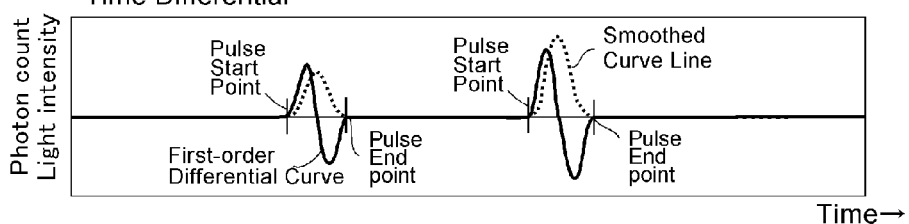
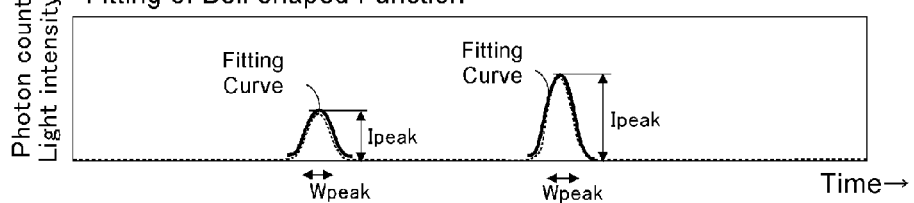

High Concentration (e. g. ~ 1nM)

Low Concentration (e. g. ~ 1pM)

OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

TECHNICAL FIELD

This invention relates to an optical analysis technique capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to an optical analysis device, optical analysis method and computer program for optical analysis, which detect individually the light from a single particle which emits light, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label or light-emitting probe has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of L), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kinjo; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.

Non-patent document 4: P. Kask, K. Palo, D. Ullmann, K. Gall PNAS 96, 13756-13761 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

In the above-mentioned scanning molecule counting method, when the counting of light-emitting particles or detection of the concentration or number density of a light-emitting particle is intended as the main purpose, more precise results will be obtained by detecting as many light-emitting particles in a solution as possible. Especially in a case of a solution with a low light-emitting particle concentration, it is preferable that a light detection region is movable along a route of a broader region or a longer distance in order to detect as many light-emitting particles as possible. In that case, in order to obtain a more reliable detected result (the detected number or number density of light-emitting particles), it should be cautious not to change the size and shape of the light detection region during the moving of the light detection region along with avoiding detecting the same light-emitting particle as different particles. [If the same light-emitting particle is detected as different particles or the size and shape of the light detection region change, the accuracy of the detected number or number density of light-emitting particles would deteriorate.]

Thus, the main object of the present invention is to provide a novel way of lowering the possibility of detecting the same light-emitting particle as different particles, and, moving a light detection region without its size or shape change to enable scanning the inside of a sample solution in a broader region or along a longer route in the above-mentioned scanning molecule counting method.

Solution to Problem

According to one aspect of the present invention, the above-mentioned object is achieved by an optical analysis device which detects light from a light-emitting particle dispersed and moving at random in a sample solution using an optical system of a confocal microscope or a multiphoton microscope, comprising: a light detection region mover which moves a position of a light detection region of the optical system of the microscope in a flat plane in the sample solution; a light detector which detects light from the light detection region; and a signal processor which generates time series light intensity data of the light from the light detection region detected with the light detector during moving the position of the light detection region in the sample solution and detects a signal indicating light from each light-emitting particle individually in the time series light intensity data; wherein the light detection region mover moves the position of the light detection region along a second route whose position moves along a first route.

In this structure, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Further, in the followings in this specification, "a signal" of a light-emitting particle means a signal expressing light from a light-emitting particle, unless noted otherwise.

As understood from the above, in the basic structure of the present invention, i.e., the scanning molecule counting method, the light detection is sequentially performed while the position of a light detection region is moved in a sample solution, namely, while the inside of the sample solution is scanned with the light detection region. Then, when the light detection region moving in the sample solution encompasses a randomly moving light-emitting particle, the light from the light-emitting particle is detected by the light detector, and thereby, it is expected that the existence of one particle will be detected. Thus, in the sequentially detected light, a signal indicating light from a light-emitting particle is individually detected, and thereby, the existences of individual particles are detected one by one, and accordingly, diverse information on the conditions of the particles in the solution will be acquired. In that case, typically, the position of the light detection region is moved in a manner that it circulates along a certain closed route, and thus, if the diffusive motion of a light-emitting particle was comparatively slow, the same light-emitting particle could be detected in every circulation. Further, when the moving route of the position of the light detection region is developed in three dimensions, the mechanism of the light detection region mover would become complicated, and the shape and size of the light detection region could be changed in accordance with the position of the light detection region in the direction of the optical axis, depending upon types of objectives. Furthermore, since the objective used in a highly sensitive confocal optical system to detect one molecule, has the short operating distance, the adjustment for a microtiter plate is difficult because, in the case of the microtiter, the direction allowing the approaching to the sample solution is limited to only the direction from the bottom of the container.

Then, in the above-mentioned inventive device, the position of the light detection region is moved along the second route whose position moves along the first route in a flat plane in the sample solution. According to this structure, because of the moving of the position of the second route along which the position of the light detection region moves, the moving route of the position of the light detection region in the sample solution does not pass through the same region at least until the completion of the moving of the position of the second route along the first route (except momentarily passed route crossings), so that the possibility of detecting the same light-emitting particle twice or more will be reduced substantially. Further, since the position of the light detection region is moved in a flat plane in the sample solution, the change in shape or size of the position of the light detection region will be suppressed to the minimum.

In the above-mentioned structure, in order to suppress the change in shape or size of the light detection region to the possible minimum, the position of the light detection region should be restricted within the range where aberration is small in the field of view of the objective. On the other hand, since the object to be observed is a light-emitting particle moving at random, it can be considered that the position of the light detection region is allowed to pass the same position after the lapse of time sufficient for a once detected light-emitting particle to diffuse and move to a different place. Then, the second route that is the track of the position of the light detection region, and the first route that is the track of the position of the second route may be cyclic routes, respectively. In that case, in order to easily grasp the track of the position of the light detection region with reference to the sample solution and easily check that the position of the light detection region does not continuously pass through the same region within a short time, the moving cycle time of the position of the light detection region along the second route may be set shorter than the moving cycle time of the position of the second route along the first route. Moreover, when the first and the second routes are set as cyclic routes, in order to prevent the position of the light detection region from passing through the same region as far as possible, preferably, the moving cycle time $\tau1$ of the position of the light detection region and the moving speed $v2$ of the position of the second route are set so that the moving cycle time $\tau1$ of the position of the light detection region, the moving speed $v2$ of the position of the second route and the diameter $d$ of the light detection region will satisfy:

$$v2\cdot\tau1>d.$$

Thereby, the second route moves at least the distance equal to the diameter of the light detection region during one circulation of the position of the light detection region along the second route, and thus, during the continuous circulations of the position of the light detection region, it will be avoided that the light detection region overlaps with the region through which it has passed in the previous circulation.

The above-mentioned moving of the position of the light detection region in the sample solution in the optical system of the confocal light microscope is concretely performable by either of the changing of the optical path of the optical system of the microscope and the moving of the container containing a sample solution. Then, in the present invention, typically, the moving along the second route of the position of the light detection region may be made by changing the optical path of the optical system of the microscope while the moving of the position of the second route along the first route may be performed by moving the position of the sample solution. In other words, according to this manner, the combination of the circulating motion of the light detection region by changing the optical path of the optical system and the circulating motion of the sample solution enables the scanning of broader area or longer distance in the sample solution. In this regard, the moving of the position of the light detection region along the second route within the sample solution by changing the optical path of the optical system of the microscope may be conducted in an arbitrary way. For example, changing the optical path of the optical system of the microscope to change the position of the light detection region may be performed using a galvanometer mirror adopted in a laser scan type light microscope. According to the manner of changing the position of the light detection region by changing the optical path of the optical system of the microscope, the moving of the light detection region is quick, and since neither mechanical vibration nor hydrodynamic action occurs substantially in the sample solution, it is advantageous to enable a measurement under a stable condition without a light-emitting particle to be an object to be detected being influenced by a dynamic action. Concretely, the second route may be circular or elliptical. On the other hand, the shape of the first route may be circular, elliptical or linear. In this regard, preferably, as already noted, the moving of the sample solution may be conducted by moving the container of the sample solution with the moving of the stage of the microscope. In that case, it is thought that, since no flow does occur in the solution, the light-emitting particle in the sample solution is less influenced.

Furthermore, in the above-mentioned device, the moving speed of the position of the light detection region in the sample solution may be appropriately changed based on the characteristic or the number density or concentration of the light-emitting particle in the sample solution. As understood in a person skilled in the art, the condition of detected light from the light-emitting particle may change in accordance with its characteristic, number density or concentration in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured precisely or with sufficient sensitivity.

Moreover, in the above-mentioned device, the moving speed of the position of the light detection region in the sample solution is preferably set to be higher than the diffusional moving velocity of a light-emitting particle (the average moving speed of a particle owing to the Brownian motion). As explained above, in the present invention, a light-emitting particle will be detected individually by detecting the light emitted from the light-emitting particle in the light detection region. However, when the light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of a light-emitting particle, and thereby it becomes possible to make one light-emitting particle associated with one signal. In this regard, since the diffusional moving velocities differ depending upon light-emitting particles, it is preferable that the moving speed of the light detection region can be changed appropriately according to the characteristics (especially, the diffusion constant) of the light-emitting particle as described above.

In the processes of the signal processor of the above-mentioned inventive device, the judgment of whether or not one light-emitting particle enters into the light detection region from a signal in the successively detected values from the light detector may be performed based on the shape of the signal in the time series light intensity data. In an embodiment, typically, it may be designed that the entry of one light-emitting particle into a light detection region is detected when a signal with a larger intensity than a predetermined threshold value is detected. More concretely, as explained in the following column of embodiments, usually, a signal indicating light from a light-emitting particle appears as a bell-shaped pulse form signal having an intensity beyond a certain degree in the time series detected values, i.e., light intensity data, of the light detector, while a noise is not of bell-shaped pulse form, or appears as a signal with a small intensity. Then, the signal processor of the inventive device may be designed to detect on time series light intensity data a pulse form signal which has an intensity exceeding a predetermined threshold value as a signal indicating light from a single light-emitting particle. The "predetermined threshold value" can be experimentally set to an appropriate value.

Furthermore, the object to be detected in the inventive device is the light from a single light-emitting particle, and thus, light intensity is extremely weak, and when one light-emitting particle is a single fluorescent molecule or several molecules, the light is stochastically emitted from the light-emitting particle, so that minute time gaps can be generated in the signal values. If such a gap is generated, the identification of a signal corresponding to the existence of one light-emitting particle will become difficult. Then, the signal processor may be designed to smooth time series light intensity data to process the data so that minute time gaps in signal values can be ignored, and to detect as a signal indicating light from a single light-emitting particle a bell-shaped pulse form signal having an intensity beyond a predetermined threshold value in the smoothed time series light intensity data.

In one of manners of the above-mentioned present invention, the number of light-emitting particles encompassed in the light detection region may be counted by counting the number of the selectively detected signals (The counting of particles). In that case, by associating the number of the detected light-emitting particles with the moving amount of the position of the light detection region, the information on the number density or concentration of the light-emitting particle identified in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining the whole volume of the moving track of the position of the light detection region by an arbitrary method, for example, by moving the position of the light detection region at a predetermined speed, the number density or concentration of the light-emitting particle can be concretely computed.

The processes of the optical analysis technique of conducting a light detection with moving the position of a light detection region in a sample solution and detecting the signal from each light-emitting particle individually in the above-mentioned inventive device, in which the position of the light detection region is moved along the second route whose position moves along the first route in a flat plane in the sample solution so that the possibility that the same light-emitting particle is detected twice or more is substantially reduced, can be realized with a general-purpose computer. Thus, according to another aspect of the present invention, there is provided a computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising: moving a position of a light detection region of the optical system of the microscope in a flat plane in the sample solution along a second route whose position moves along a first route in a flat plane in the sample solution; detecting light from the light detection region and generating time series light intensity data during the moving of the position of the light detection region; and detecting individually a signal indicating light from each light-emitting particle using the time series light intensity data. In this regard, the computer program is provided with being stored in a computer readable storage medium. The computer reads out the program memorized in the storage device and realizes the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

Also in this computer program, preferably, the first and the second route are cyclic routes, and the moving cycle time of the position of the light detection region along the second route is set shorter than the moving cycle time of the position of the second route along the first route. Further, in that case, it is preferable that the moving cycle time $\tau1$ of the position of the light detection region, the moving speed $v2$ of the position of the second route and the diameter $d$ of the light detection region are set to satisfy:

$$v2\cdot\tau1 > d.$$

And, the moving of the position of the light detection region along the second route may be performed by changing the optical path of the optical system while the moving of the position of the second route in the sample solution along the first route may be performed by moving the position of the sample solution. In that case, for the moving of the position of the light detection region within the sample solution by changing the optical path of the optical system, for example, the optical path of the optical system of the microscope may be changed to change the position of the light detection region using a galvanometer mirror adopted in a laser scan type light microscope. Also, the second route may be circular or elliptical and the first route may be circular, elliptical or linear. Furthermore, the moving speed of the position of the light detection region in the sample solution may be appropriately changed based on the characteristics, the number density or concentration of the light-emitting particle in the sample solution. Preferably, the moving speed of the position of the light detection region in the sample solution is set higher than the diffusion moving velocity of the light-emitting particle to be the object to be detected.

Moreover, in the above-mentioned computer program, individual detection of a signal indicating light from each light-emitting particle may be performed based on the shape of the time series signals. In one embodiment, typically, it may be designed that the entry of one light-emitting particle into the light detection region is detected when a signal with a larger intensity than a predetermined threshold value is detected. Concretely, a bell-shaped pulse form signal having an intensity beyond a predetermined threshold value in light intensity data may be detected as a signal indicating light from a single light-emitting particle, and preferably, the time series light intensity data may be smoothed so that a bell-shaped pulse form signal having an intensity beyond a predetermined threshold value in the smoothed time series light intensity data may be detected as a signal indicating light from a single light-emitting particle.

Also in this computer program, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles.

According to the above-mentioned inventive device or computer program, there is realized a novel optical analysis method of conducting detection of the light of each light-emitting particle with moving the position of a light detection region in a sample solution, in which method, the position of the light detection region is moved along the second route whose position moves along the first route in a flat plane in a sample solution, thereby lowering the possibility of detecting the same light-emitting particle twice or more substantially. Thus, according to the present invention, there is further provided an optical analysis method of detecting light from a light-emitting particle dispersed and moving at random in a sample solution using an optical system of a confocal microscope or a multiphoton microscope, comprising steps of: (a) moving a position of a light detection region of the optical system of the microscope in a flat plane in the sample solution; (b) detecting light from the light detection region and generating time series light intensity data during the moving of the position of the light detection region; and (c) detecting individually a signal indicating light from each light-emitting particle using the time series light intensity data, wherein in the step (a), the light detection region is moved along a second route whose position moves along a first route.

Also in this method, preferably, the first and the second route are cyclic routes, and the moving cycle time of the position of the light detection region along the second route is set shorter than the moving cycle time of the position of the second route along the first route. Further, in that case, it is preferable that the moving cycle time $\tau1$ of the position of the light detection region, the moving speed $v2$ of the position of the second route and the diameter $d$ of the light detection region are set to satisfy:

$$v2\cdot\tau1 > d.$$

And, the moving of the position of the light detection region along the second route may be performed by changing the optical path of the optical system while the moving of the position of the second route in the sample solution along the first route may be performed by moving the position of the sample solution. In that case, for the moving of the position of the light detection region within the sample solution by changing the optical path of the optical system, for example, the optical path of the optical system of the microscope may be changed to change the position of the light detection region using a galvanometer mirror adopted in a laser scan type light microscope. Also, the second route may be circular or elliptical and the first route may be circular, elliptical or linear. Furthermore, the moving speed of the position of the light detection region in the sample solution may be appropriately changed based on the characteristics, the number density or concentration of the light-emitting particle in the sample solution. Preferably, the moving speed of the position of the light detection region in the sample solution is set higher than the diffusion moving velocity of the light-emitting particle to be the object to be detected.

Moreover, in the above-mentioned method, individual detection of a signal indicating light from each light-emitting particle may be performed based on the shape of the time series signals. In one embodiment, typically, it may be designed that the entry of one light-emitting particle into the light detection region is detected when a signal with a larger intensity than a predetermined threshold value is detected.

Concretely, a bell-shaped pulse form signal having an intensity beyond a predetermined threshold value in light intensity data may be detected as a signal indicating light from a single light-emitting particle, and preferably, the time series light intensity data may be smoothed so that a bell-shaped pulse form signal having an intensity beyond a predetermined threshold value in the smoothed time series light intensity data may be detected as a signal indicating light from a single light-emitting particle.

Also in this method, there may be comprised a step of (d) counting the number of the light-emitting particles detected during the moving of the position of the light detection region by counting the number of the signals from the light-emitting particles detected individually and/or a step of (e) determining the number density or concentration of the light-emitting particle in the sample solution based on the number of the detected light-emitting particles.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Thus, in the scanning molecule counting method by the above-mentioned present invention, the moving track of the position of a light detection region, i.e., the scanning route in a sample solution, is improved so that detecting the same light-emitting particle as different particles and change in shape or size of the light detection region will be avoided as far as possible, and thereby the scanning in the sample solution is performed in a broader region or along a longer distance so that the prevention of deterioration of the accuracy of the detected number or number density of light-emitting particles will be achieved. Actually, in a case of light-emitting particles having a low diffusional speed, when the position of a light detection region is moved along one cyclic route, the same particle can be periodically detected multiple times unintentionally and there have occurred the deterioration of the accuracy of the detected number of particles and the enlargement of the scattering of result values due to detecting the signals from the same particle as those from different particles or due to the bleaching of a light-emitting particle (see the embodiment). (However, it is also possible to improve the accuracy in the detection of a characteristic of a particle by carrying out multiple times detection of the same particle intentionally.) According to the present invention, different regions in a sample solution will be scanned with a light detection region during moving its position except at the crossings of the route, so that the possibility of detecting the same light-emitting particle as different particles can be substantially reduced; the scattering in the detected number of particles can be reduced or the influence of the bleaching of a light-emitting particle can be suppressed to the minimum (see the embodiment.).

Other purposes and advantages of the present inventions will become clear by explanations of the following preferable embodiments of the present invention.

BRIEF DESCRIPTIONS OF DRAWINGS

Figure 1B:
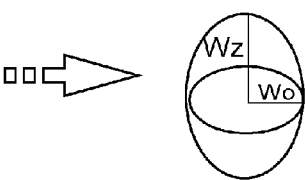
Figure 1C:
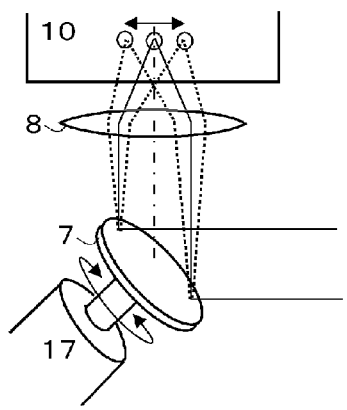
Figure 1D:
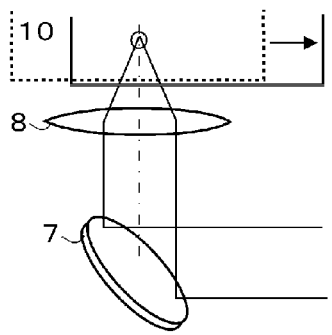

FIG. 1A is a schematic diagram of the internal structure of the optical analysis device with which the scanning molecule counting method according to the present invention is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution. FIG. 1D is a schematic diagram of the mechanism which moves the horizontal position of a micro plate to move the position of a sample solution.

FIGS. 2A and 2B are a schematic diagram explaining the principle of the light detection and a schematic diagram of the variation of the measured light intensity with time in the scanning molecule counting method to which the present invention is applied, respectively. FIG. 2C is a drawing explaining about the manner of moving the position of the light detection region along the scanning track (the second route) by changing the optical path of the optical system in the present invention. FIG. 2D is a drawing explaining about the manner of moving the position of a sample solution (moving the position of the second route along the first route). FIG. 2E is a drawing explaining about the relation between the moving of the position of a sample solution and the moving of the position of the light detection region along the scanning track.

FIG. 3 are diagrams showing the procedures of the scanning molecule counting method performed in accordance with the present invention in the form of a flow chart.

FIGS. 4A and 4B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 4C shows drawings explaining an example of the signal processing step of the detected signals in the procedure for detecting the existence of a light-emitting particle from the measured time series light intensity data (change in time of photon count) in accordance with the scanning molecule counting method.

Figure 5:
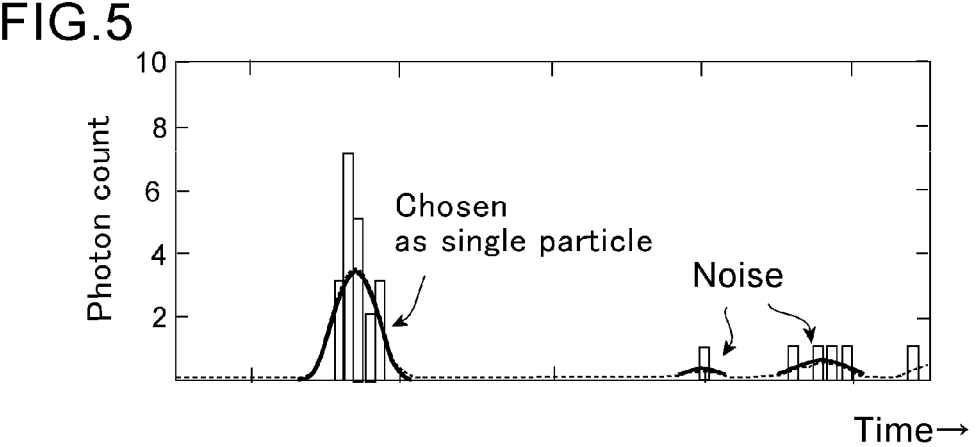

FIG. 5 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or a contaminant.

Figure 6A:
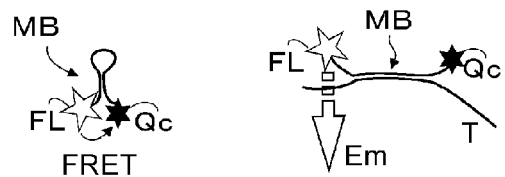
Figure 6B:
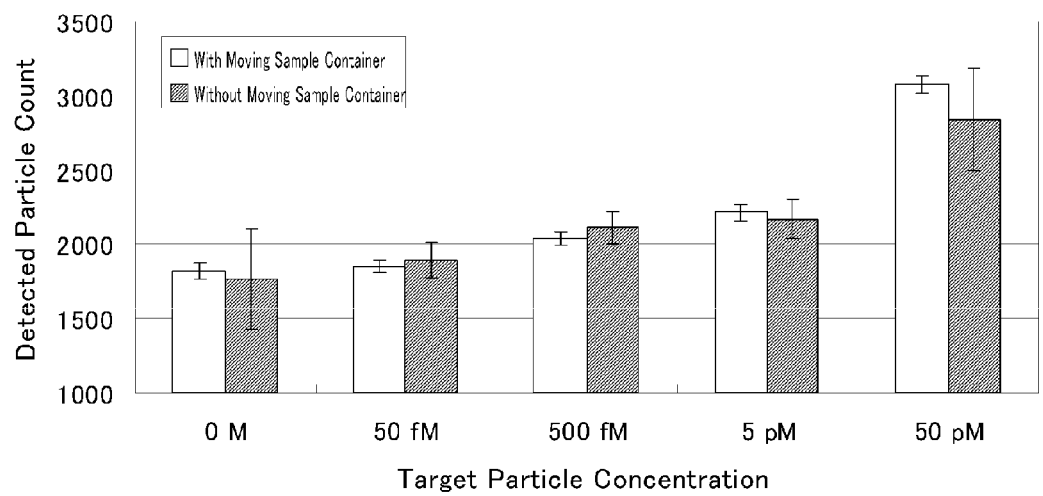
Figure 6C:
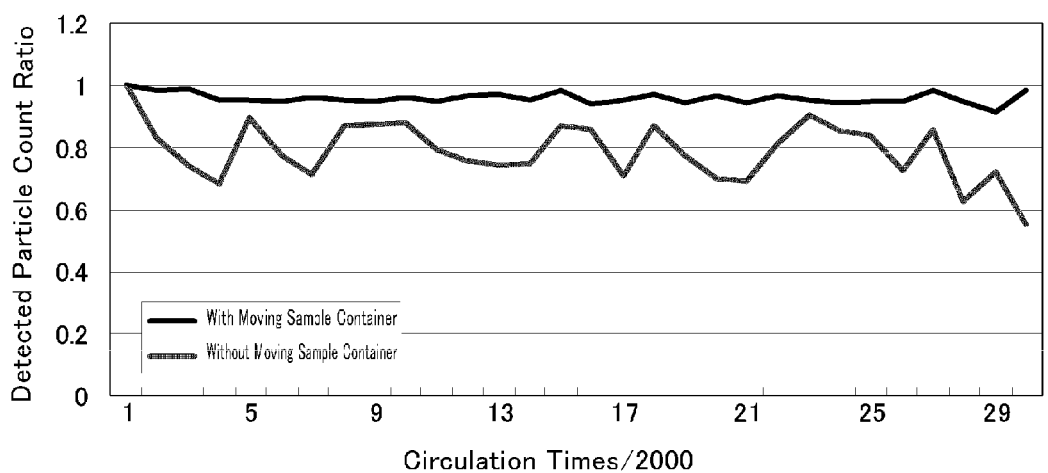

FIG. 6A is a schematic diagram of a morphological change of a molecule in a binding reaction of nucleic acids using a molecular beacon observed in Embodiment 1. FIG. 6B shows the particle counts detected by the scanning molecule counting method in changing the target particle concentration in the solution of the reaction system of FIG. 6A. "With moving a sample container" indicates cases that the moving of the position of the light detection region by changing an optical path and the moving of the moving track of the position of the light detection region were simultaneously performed by moving a sample container according to the teaching of the present invention, and "Without moving a sample container" indicates cases that only the moving of the position of the light detection region by changing an optical path was performed. Bar graphs and error bars are the average values and CV values in 20 seconds×30 measurements, respectively. FIG. 6C shows the variation of the number of light-emitting particles detected per 1 time measurement (for 20 seconds) in the case of light measurements of 20 seconds×30 times were conducted continuously.

Figure 7A:
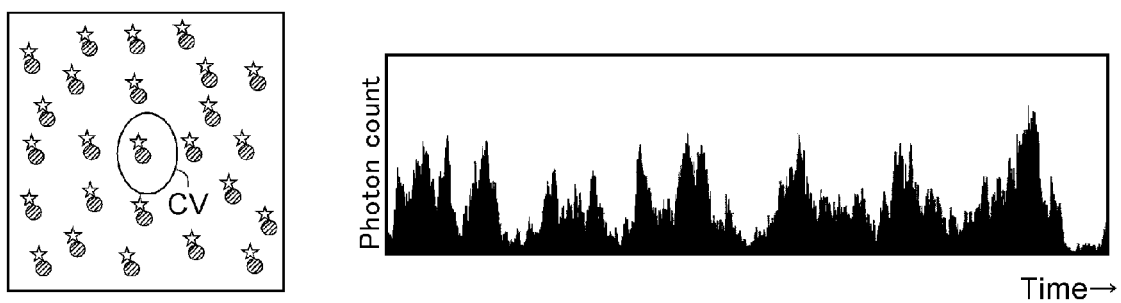
Figure 7B:
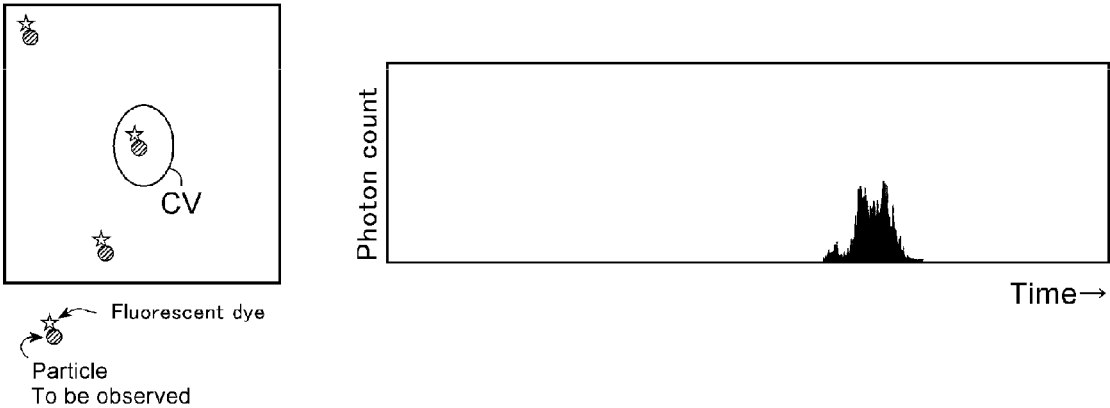

FIGS. 7A and 7B show examples of the time variation of the photon count (light intensity) obtained in a conventional optical analysis technique computing fluorescence intensity fluctuation, where FIG. 7A shows a case that the particle concentration is at a level providing a sufficient precision in the measurement, and FIG. 7B shows a case that the particle concentration in a sample is significantly lower than the case of FIG. 7A.

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
14a - - - Dichroic mirror or Polarization beam splitter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.
Structure of Optical Analysis Device
In the basic structure, an optical analysis device which realizes the optical analysis technique according to the present invention is a device constructed by associating the optical system of a confocal microscope and a photodetector, enabling FCS, FIDA, etc., as schematically illustrated in FIG. 1A. Referring to this drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically fluorescent particles or particles to which a light emitting label such as a fluorescent dye is attached, are dispersed or dissolved, and when such a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13; transmits through the barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this optical analysis device (typically, the light intensity is spread in accordance with a Gaussian type distribution having the peak at the center of the region. The effective volume is a volume of an approximate ellipsoid bordering a surface where the light intensity is reduced to $1/e^2$ of the peak intensity.), which focal region is called as "confocal volume". Furthermore, in the present invention, since the light from a single light-emitting particle, for example, the faint light from one fluorescent dye molecule is detected, preferably, a super high sensitive photodetector, usable for the photon counting, is used for the photodetector 16. When the detection of light is performed by the photon counting, the measurement of light intensity is performed for a predetermined time in a manner of measuring the number of photons which have sequentially arrived at a photodetector in every predetermined unit time (BIN TIME). Thus, in this case, the time series light intensity data is time series photon count data. Also, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, quick measurement can be achieved even when there are two or more specimens.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (the type of changing an optical path to move the absolute position of a light detection region). This mirror deflector 17 may be the same as that of a galvanomirror device equipped on a usual laser scan type microscope. Furthermore, as illustrated in FIG. 1D, the stage position changing apparatus 17a is operated in order to move the horizontal position of the container 10 (micro plate 9), into which the sample solution has been dispensed, to move the relative position of the light detection region in the sample solution (the type of moving the position of a sample solution). As explained in detail later, in the present invention, the light detection region is moved to circulate along a scanning track (the second route) by the above-mentioned type of moving the absolute position of the light detection region by changing optical path while the position of the scanning track of the light detection region in the sample solution is moved along a predetermined moving track (the first route) by the type of moving the position of a sample solution simultaneously. In either of the ways, in order to attain a desired moving pattern of the position of the light detection region, the mirror deflector 17 and the stage position changing apparatus 17a are driven in harmony with the light detection of the photodetector 16 under the control of the computer 18. The scanning track of the position of the light detection region may be a closed cyclic route of a circle or an ellipse, etc., and the moving track of the position of the sample solution may be arbitrarily selected from circular, elliptical, straight and curvilinear ones, or a combination of these (The program in the computer 18 may be designed so that various moving patterns can be selected.)

In the case that a light-emitting particle to be an object to be observed emits light by multiple photon absorption, the above-mentioned optical system is used as a multiphoton microscope. In that case, since the light is emitted only from the focal region of the excitation light (light detection region), the pinhole 13 may be removed. Further, in the case that a light-emitting particle to be an object to be observed emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, it may be designed to divide a detected light into two or more wavelength bands by inserting a dichroic mirror 14a in a detected light optical path, and detect them independently with two or more photodetectors 16. According to this structure, it becomes possible to detect the information on the emission wavelength characteristic (emission spectrum) of a light-emitting particle or detect the lights of two or more kinds of light-emitting particles, when contained, independently in accordance with the wavelengths. Moreover, with respect to the light detection, it may be designed to use light, polarized in a predetermined direction, as excitation light and detect separately components of detected light in the direction of the excitation light and the direction perpendicular thereto, so as to detect the polarization characteristics of the light of a light-emitting particle. In that case, a polarizer (not shown) is inserted in an excitation light optical path, and a polarization beam splitter 14a is inserted in a detected light optical path.

The computer 18 has a CPU and a memory, and the inventive procedures are performed through the CPU executing various operational processes. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disc, a magnetic optical disk, a CD-ROM, a DVD-ROM, a semiconductor memory, etc., or the above-mentioned program may be distributed to a computer through communication line, and the computer which received this distribution may be made to execute the program.

The Principle of the Inventive Method

As described in the column of "Summary of Invention", briefly, in the inventive optical analysis technique, in the scanning molecule counting method, the scanning track of the position of a light detection region is moved in a flat plane in a sample solution during the moving of the position of the light detection region so as to prevent the light detection region from passing through the same region in a short time as far as possible, thereby avoiding the detecting of the same light-emitting particle as different particles and the change in size or shape of the light detection region as far as possible, and thus, it is tried to suppress the scattering in the detected number of light-emitting particles and improve the detection accuracy. In the following, the principle of the scanning molecule counting method and the manners of the circulating movements of a light detection region in the present invention are explained.

1. Principle of Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques, such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 7A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn on FIG. 7B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring time should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA.

As the processes to be performed in the scanning molecule counting method, briefly speaking, the light detection is performed together with moving the position of the light detection region CV in a sample solution, namely, scanning the inside of the sample solution with the light detection region CV by driving the mechanism for moving the position of the light detection region to change the optical path as schematically drawn in FIG. 2A. Then, for example, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. Moreover, from the signal intensities, the characteristics of the lights of various light-emitting particles and the characteristics of light-emitting particle itself become detectable for the respective light-emitting particles. In the principle of the scanning molecule counting method, no statistical calculation processes, such as the calculation of the fluorescence intensity fluctuation, are conducted and the light-emitting particles are one by one detected, and therefore, the information about the concentration or number density, characteristics of the particle is acquirable even in a sample solution with a low particle concentration at the level where no sufficiently accurate analysis is available in FCS, FIDA, etc.

2. Scanning Track of Light Detection Region

In the above-mentioned scanning molecule counting method, as explained in detail later, preferably, the position of the light detection region is moved at a higher speed than the moving speed of the Brownian motion (diffusion moving velocity) of a light-emitting particle. Further, for the stability of light-emitting particles and other substances, turbulences, such as flow, vibration, etc. in a sample solution should be suppressed to the minimum. Therefore, principally, it is preferable that the moving of the position of a light detection region is performed by changing the optical path of the optical system of a microscope. This is because, as explained above, according to the changing the optical path with the mirror deflector 17, the moving of the position of a light detection region is comparatively easily executable at a high speed. In this respect, near the circumference of the field of view of an objective, generally, the aberration becomes large so that the size and shape of the light detection region may be changed depending upon places, and therefore, it is preferable that the moving range of the position of the light detection region by changing the optical path is within an area around the center of the field of view of the objective with little aberration. However, when the moving range of the position of a light detection region is restricted to the area around the center of the field of view of the objective, the region through which the light detection region passes, i.e., the scanning region, becomes small so that the detected number of light-emitting particles may be decreased. Further, when a small region is repetitively passed through, especially for a slowly diffusing particle, the light detection region will repetitively pass through the region occupied by the particle, so that the same particle could be detected multiple times. In this connection, although, through conducting intentionally the repetitive detections of the light from the same particle, it is useful to estimate precisely a characteristic of light of the particle, it is preferable that a wider region or a longer distance can be scanned without multiple times detection of the same particles when it is wanted to increase the detected number of light-emitting particles as much as possible for counting the number, detecting the concentration or number density of light-emitting particles, etc. Moreover, in that case, when it is wanted to acquire the information about a light-emitting particle concentration, it is preferable that the size and shape of the light detection region are hardly changed so that the length or volume of the scanned region (the passing region of the light detection region) can be easily estimated.

Thus, in the present invention, considering the requests with respect to the moving of the position of a light detection region in the scanning molecule counting method as described above, in order to enable the stable scanning of a broader area or a longer distance, as already noted, the moving track of the position of a light detection region is improved such that the position of the light detection region is moved along a predetermined scanning track while the scanning track is moved in a two-dimensional flat plane so as to avoid the position of the light detection region passing through the same region (except the crossings of the route) within a short time as far as possible.

Concretely, first, by driving the mirror deflector 17 in FIG. 1A to change the optical path, the circulating movement of a light detection region is carried out along a scanning track (the second route) in the field of view of an objective, as shown in FIG. 2C. And, simultaneously with this movement, the stage position changing apparatus 17a is driven continuously to move the position of the sample solution as shown in FIG. 2D, thereby moving the position of the scanning track of the light detection region with reference to the sample solution, so that it is avoided as far as possible that the light detection region scans the same region within a short time. [As in FIG. 2D, when the position of a sample solution is moved in a cyclic route, after one cycle of circulation of the position of the scanning track of the light detection region along the cyclic route, the light detection region will start scanning the same region again; however, during one round of the position of the scanning track of the light detection region, usually, it can be considered that the light-emitting particle is moved to a different place owing to diffusion, and thus, the possibility that the same light-emitting particle will be detected again can be considered to be very low.]

In this regard, it is desired that the speed of the light detection region with reference to the sample solution is almost constant so that the pulse form shape of a signal of light of a light-emitting particle will be always constant, but when the moving speed of the position of the sample solution is high to the extent equal to the moving speed of the light detection region along the scanning track, the speed of the light detection region with reference to the sample solution would be changed. Thus, preferably, the moving speed of the position of the sample solution is low enough as compared with the moving speed of the light detection region along the scanning track (for example, 20% or less). Also, as shown in FIG. 2E, after the light detection region has moved the scanning track one cycle, in order to avoid overlapping the region through which the light detection region will passes in this circulation time (ii) on the region through which it has passed in the previous circulation time (i), the moving speed of the position of the sample solution (the moving speed of the position of the scanning track) v2 and the moving cycle time τ1 of the light detection region in the scanning track are set to satisfy:

$$v2 \cdot \tau1 > d \tag{1},$$

in the relation with the diameter d of the light detection region. Concretely, supposing the diameter d of the light detection region is 0.4~30 μm and the moving cycle time τ1 of the light detection region in the scanning track is 0.6~600 mseconds, the moving speed v2 of the position of the sample solution is to become 0.67 μm/second or more. Actually, the moving cycle time τ1 in the scanning track of the light detection region is usually set to 6~60 mseconds, and thus, in that case, the moving speed v2 of the position of the sample solution will become 17 μm/second or more. Since the moving speed of the light detection region in the scanning track is typically set in 10~90 mm/second, the moving speed v2 of the position of the sample solution is so small that it can almost be disregarded.

Operation Processes of Scanning Molecule Counting Method

In the embodiment of the scanning molecule counting method in accordance with the present invention with the optical analysis device 1 as illustrated in FIG. 1A, concretely, there are conducted (1) a preparation of a sample solution containing light-emitting particles; (2) a process of measuring the light intensity of the sample solution and (3) a process of analyzing measured light intensities. FIG. 3 shows the processes in this embodiment in form of the flow chart.

(1) Preparation of a Sample Solution

The particle to be an observed object in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecules. When the particle to be an observed object is a particle which emits no light, there is used a particle to which a light emitting label (a fluorescence molecule, a phosphorescence molecule, and a chemiluminescent or bioluminescent molecule) is attached in an arbitrary manner. Typically, the sample solution is an aqueous solution, but not limited to this, and it may be an organic solvent or other arbitrary liquids.

(2) Measurement of Light Intensity of a Sample Solution (FIG. 3—Step 100)

The measurement of the light intensity in the optical analysis by the scanning molecule counting method of the present embodiment may be conducted in a manner similar to a measurement process of light intensity in FCS or FIDA except that the mirror deflector 17 and the stage position changing apparatus 17a are driven to move the position of the light detection region within the sample solution (scanning the sample solution) and move the sample solution during the measurement. In the operation processes, typically, after dispensing a sample solution into the well(s) 10 of the micro plate 9 and putting it on the stage of the microscope, when a user inputs to the computer 18 a command of staring a measurement, the computer 18 executes programs memorized in a storage device (not shown) (the process of moving the position of the light detection region in the sample solution, and the process of detecting light from the light detection region during the moving of the position of the light detection region) to start radiating the excitation light and measuring the light intensity in the light detection region. During this measurement, under the control of the operation process of the computer 18 according to the programs, the mirror deflector 17 drives the mirror 7 (galvanomirror) to perform the circulating movement of the position of the light detection region along a scanning track in the well 10 while the stage position changing apparatus 17a moves the position of the micro plate 9 on the stage of the microscope. Simultaneously with this, the photodetector 16 sequentially converts the detected light into electric signals and transmits it to the computer 18, which generates the time series light intensity data from the transmitted signals and stores it in an arbitrary manner. Then, these processes are performed for arbitrary time and one measurement is completed. In this regard, the photodetector 16 is typically a super high sensitive photodetector which can detect an arrival of a single photon, and thus when the detection of light is performed by the photon counting, the time series light intensity data may be time series photon count data.

The moving speed of the position of the light detection region in the circulating movement along a scanning track during the measurement of the light intensity may be a predetermined velocity set arbitrarily, for example, experimentally or in order to meet the purpose of an analysis. In a case of acquiring the information on the number density or concentration based on the number of detected light emitting particles, the region size or volume through which the light detection region has passed is required, and therefore, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

The moving speed of the position of the light detection region is preferably set to a value quicker than the moving speed in the random motion, i.e., the Brownian motion of a light-emitting particle in order to perform quantitatively precisely individual detection of a light-emitting particle to be observed from the measured time series light intensity data or the counting of the number of light-emitting particles, while satisfying the condition of the above-mentioned Expression (1). Since the particle to be observed in the inventive optical analysis technique is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 4A, whereby the light intensity changes at random (As noted, the excitation light intensity in the light detection region is reduced from the peak at the center of the region toward its outside.), so that it would become difficult to determine a significant light intensity change corresponding to each light-emitting particle. Then, preferably, as drawn in FIG. 4B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each light-emitting particle becomes almost uniform in the time series light intensity data as illustrated in the most upper row of FIG. 4C (When a light-emitting particle passes through the light detection region in an approximately straight line, the profile of the light intensity change forms a bell shape similar to the excitation light intensity distribution.) and the correspondence between each light-emitting particle and light intensity can be easily determined.

Concretely, the time $\Delta t$ required for a light-emitting particle having a diffusion coefficient D to pass through the light detection region of radius Wo (confocal volume) by the Brownian motion is given from the equation of the relation of mean-square displacement:

$$(2Wo)^2 = 6D \cdot \Delta t \qquad (2)$$

as:

$$\Delta t = (2Wo)^2 / 6D \qquad (3),$$

and thus, the velocity of the light-emitting particle moving by the Brownian motion (diffusional moving velocity) Vdif, becomes approximately $$Vdif = 2Wo/\Delta t = 3D/Wo \qquad (4)$$

Then, with reference to this, the moving speed of the position of the light detection region may be set to a value sufficiently quicker than Vdif. For example, when the diffusion coefficient of a particle to be observed is expected to be about $D=2.0\times10^{-10}$ m²/s, Vdif will be $1.0\times10^{-3}$ m/s, supposing Wo is about 0.62 μm, and therefore, the moving speed of the position of the light detection region may be set to its 10 times or more, 15 mm/s, etc. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of the light intensity variation becomes an expected profile (typically, similar to the excitation light intensity distribution).

(3) Analysis of Light Intensity

When the time series light intensity data of the light-emitting particles in the sample solution is obtained by the abovementioned processes, there are performed the detection of a signal corresponding to the light from a light-emitting particle on light intensity data, analyses, such as concentration calculation, etc. in the computer 18 through processes in accordance with programs memorized in a storage device.

(i) Detection of a Signal Corresponding to a Light-Emitting Particle

When the track of one light-emitting particle in its passing through the light detection region is approximately straight as shown in FIG. 4B, the light intensity variation in the signal corresponding to the particle in the time series light intensity data has a bell shaped profile reflecting the light intensity distribution in the light detection region (determined by the optical system) (See FIG. 4C, the most upper row). Thus, basically in the scanning molecule counting method, when the time width for which the light intensity value exceeding an appropriately set threshold value continues is in a predetermined range, the signal having the profile of the light intensity may be judged to correspond to one particle having passed through the light detection region, and thereby one light-emitting particle is detected. And a signal whose time width in which light intensity beyond the threshold value continues is not within the predetermined range is judged as noise or a signal of a contaminant. Further, when the light intensity distribution in the light detection region can be assumed as a Gaussian distribution:

$$I=A\cdot\exp(-2t^2/a^2) \quad (5),$$

and when the intensity A and the width a, computed by fitting Expression (5) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

As an example of the process of the collective detection of light-emitting particles in time series light intensity, first, a smoothing treatment is performed to the time series light intensity data (FIG. 4C, the most upper row "detected result (unprocessed)") (FIG. 3—step 110, FIG. 4C mid-upper row "smoothing"). Although the light emitted by a light-emitting particle is stochastic so that minute time gaps will be generated in data values, such gaps in the data values can be disregarded by the smoothing treatment. The smoothing treatment may be done, for example, by the moving average method, etc. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the smoothed time series light intensity data is computed (step 120). As illustrated in FIG. 4C, the mid-low row "time differential", in the time differential value of time series light intensity data, the value variation increases at the time of the signal value change, and thereby, the start point and the end point of a significant signal can be determined advantageously by referring to the time differential value.

After that, significant pulse signals are detected sequentially on the time series light intensity data, and it is judged whether or not each detected signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 4C, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically Gauss function as in Expression (5), it may be Lorentz type function. Then, it is judged whether or not the computed parameters of the bell shaped function are within the respective ranges assumed for the parameters of the bell-shaped profile drawn by a pulse signal to be detected when one light-emitting particle passes through the light detection region, namely, whether or not the peak intensity, pulse width and correlation coefficient of a pulse are in the respective predetermined ranges, e.g. whether or not the following conditions are satisfied:

20 μsec.<pulse width<400 μsec.

Peak intensity>1.0[*pc*/10 μsec.]

Correlation coefficient>0.95  (A)

(Step 150). Accordingly, the signal, whose computed parameters of the bell-shaped function are judged to be within the ranges assumed in a light signal corresponding to one light-emitting particle, as shown in FIG. 5 left, is judged as a signal corresponding to one light-emitting particle, and thereby one light-emitting particle has been detected. On the other hand, a pulse signal, whose computed parameters of the bell-shaped function are not within the assumed ranges, as shown in FIG. 5 right, is disregarded as noise.

The searching and judging of a pulse signal in the above-mentioned processes of steps 130-150 may be repetitively carried out throughout time series light intensity data (step 160). In this connection, the processes for detecting individually a signal from the time series light intensity data may be performed by an arbitrary way, other than the above-mentioned procedures.

(ii) Determination of Light-Emitting Particle Concentration

Further, the number of light-emitting particles may be determined by counting the number of signals of detected light-emitting particles (Counting of light-emitting particles). Also, when the volume of the whole region through which the light detection region has passed is computed out by an arbitrary way, the number density or concentration of the light-emitting particle in the sample solution can be determined from the number of light-emitting particles and the volume (Step 170).

The volume of the whole region through which the light detection region has passed may be theoretically computed out with the wavelength of excitation light or detected light, the numerical aperture of lenses and the adjustment condition of the optical system, but the volume may be determined experimentally, for instance, using the number of light-emitting particles detected by performing, with a solution having a known light-emitting particle concentration (a reference solution), the light intensity measurement, detection of (a) light-emitting particle(s) and their counting under the same condition as the measurement of a sample solution to be tested, and the light-emitting particle concentration of the reference solution. Concretely, for example, supposing the number of detected light-emitting particles is N in a reference solution of the light-emitting particle concentration C, the whole volume Vt of the region through which the light detection region has passed is given by:

$$Vt = N/C \qquad (6).$$

Alternatively, by preparing the plurality of solutions of different light-emitting particle concentrations and performing the measurement for each of the solutions, the average value of the computed Vts may be employed as the whole volume Vt of the region though which the light detection region has passed. Then, when Vt is given, the concentration c of the light-emitting particle of the sample solution, whose counting result of the light-emitting particles is n, is given by:

$$c = n/Vt \qquad (7)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage device of the computer 18 the information on the relations (Expression (6)) between concentrations C and light-emitting particle numbers N of various standard light-emitting particles for assumed moving patterns of the light detection region, so that a user of the device can appropriately use the memorized information on the relation in conducting an optical analysis.

Thus, in the scanning molecule counting method which scans in a sample solution with a light detection region and detects light-emitting particles individually, the counting of the light-emitting particles, the determination of their concentration, etc. in the sample solution can be performed through the above-mentioned procedures.

(iii) Determination of Various Characteristics

When the detection of a light-emitting particle signal has been done, it becomes possible to acquire, using the signal intensity value, information (the feature quantity of a signal) related to various characteristics of the light of the light-emitting particle or the characteristics of the light-emitting particle itself, other than the light-emitting particle concentration. For instance, in the measurement of detected light, in which a detected light is measured in each polarization direction independently and light intensity data are generated for each of the polarization directions, an arbitrary index value indicating polarization characteristics, such as a polarization degree and polarization anisotropy, can be computed from the intensity values of signals acquired from those respective light intensity data so that, from such an index value, an index value of the rotatory diffusion characteristics of the light-emitting particle can be computed. Furthermore, in the measurement of detected light, in which components of a plurality of wavelength bands in a detected light are separately measured and light intensity data are generated for each of the wavelength bands, it becomes possible to acquire information (e.g., intensity ratio in two or more wavelengths) on the emission wavelength spectrum of a light-emitting particle from the intensity values of the signals acquired from those light intensity data. Here, it should be understood that, in the scanning molecule counting method that the present invention is directed to, the information on the characteristics of light of a light-emitting particle, the characteristics of light-emitting particle itself as above can be determined for each light-emitting particle.

Thus, according to the above-mentioned present invention, the information on the number density and concentration of a light-emitting particle in a sample solution or information on other characteristics will be acquired in the scanning molecule counting method. In particular, in the present invention, as already noted, with respect to the above-mentioned moving of the position of the light detection region, the position of the light detection region is moved along a scanning track while the position of the scanning track of the position of the light detection region in a sample solution is moved by moving the position of the sample solution in the two-dimensional flat plane in the sample solution, and thereby the change of the shape and size of the light detection region is suppressed to the minimum, and also, it is avoided that the light detection region repetitively passes through the same region within a short time period. And, this structure significantly reduces the possibility of unintentional detecting the same light-emitting particle twice or more, enabling the detection of as many light-emitting particles as possible in a broader region and trying the improvement in the accuracy of the detected result.

In order to verify the validity of the present invention explained above, the experiments described below were conducted. In this regard, it should be understood that the following embodiments illustrate the validity of the present invention only, not intended to limit the scope of the present invention.

Embodiment 1

In detecting signals of light-emitting particles and counting the number of the signals in accordance with the above-mentioned scanning molecule counting method, the evaluation about the relation between the manner of moving of the position of a light detection region and the number of detected signals was conducted. In the experiment, it was verified that a nucleic acid molecule having a specific base sequence could be detected using a molecular beacon. The molecular beacon is a nucleic acid molecule in which a molecule to be a fluorescent dye FL functioning as the donor and a molecule Qc functioning as the acceptor in a fluorescence energy transfer phenomenon are attached on the respective ends. In a single form as schematically drawn in the left of FIG. 6A, the donor dye FL and the acceptor molecule Qc are close in the distance so that a fluorescence energy transfer phenomenon FRET from the donor dye to the acceptor dye occurs, while, when it binds with a nucleic acid or a nucleic acid analogue T having a base sequence complementary to the base sequence of the molecular beacon, the distance between the donor dye FL and the acceptor molecule Qc is made increase as schematically drawn on the right of FIG. 6A so that the fluorescence energy transfer phenomenon no longer occurs. In the present embodiment, for the donor dye, ATTO647N was used, and for the acceptor molecule, BHQ2, a quenching molecule absorbing the fluorescence of ATTO647N was used. Thus, in a single molecular beacon, the fluorescence of ATTO647N is absorbed by BHQ2 because of the fluorescence energy transfer phenomenon so that no fluorescence will be emitted, while, when the molecular beacon binds with a nucleic acid to be a target, the distance between the donor dye and the acceptor molecule increases so that the fluorescence Em will be emitted and detectable.

The sample solutions were prepared as follows:
(Preparation of a Nucleic Acid to be a Target of a Molecular Beacon)

k-Ras gene was artificially synthesized, inserted into a plasmid and prepared with cloning (the synthesis and preparation were ordered to Hokkaido System Science). PCR amplification was conducted, using the synthesized plasmid as a template (a template in which k-RasWt sequence was inserted into pUC57 vector), with 10000 copies of k-Ras plasmids, 0.1 μM FwPrimer (Fasmac), 0.1 μM RePrimer (Fasmac), 0.125U PrimeStar Taq (TaKaRa, R010A), 1× PrimeStar Buffer, 800 mM dNTPs and 2% DMSO, in 10 μL of a reaction capacity through thermal cycles of (10 seconds at 98° C. to 3 minutes 72° C.)×35 cycles. Then, the PCR product was purified with Wizard SV Gel and PCR Clean-Up system (Promega, A9281), preparing nucleic acids having a target sequence. In this connection, the FwPrimer (for kRas gene amplification) has the base sequence of sequence No. 1; the RePrimer (for kRas gene amplification) has the base sequence of sequence No. 2; and the template in which k-RasWt sequence has been inserted into pUC57 vector has the base sequence of sequence No. 3.

(Hybridization Reaction)

Molecular beacon, i.e., DNA having the base sequence of sequence No. 4 and in which ATTO647N was labeled to the 5' end and BHQ2 was labeled to the 3' end (83b, 20 pM, Sigma Genosis), was mixed with the template (0-50 pM) which had been obtained through PCR-amplification and purification of the plasmid into which k-Ras gene was inserted, and its annealing was conducted for 2 minutes at 95° C. and 3 hours at 60° C. in Tris buffer (10 mM Tris-HCl (pH 8.0), 400 mM NaCl, 0.1% PluronicF-127, 10% dextran sulfuric acid), and the preparation was stored at 10° C. and collected.

In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) was acquired for the above-mentioned sample solution in accordance with the manner explained in the above-mentioned "(2) Measurement of Light Intensity of a Sample Solution". In that time, a 633-nm laser light (600 μW) was used for excitation light, and, using a band pass filter, the light of the wavelength bands, 660 to 710 nm, was measured. The scanning track of the position of the light detection region in the sample solution was a circle of about 50 micrometers in diameter; the moving speed was 15 mm/sec.; the cycle time of the circulating movement was 10 m seconds (=6000 rpm); and the position of the sample container was moved at the moving speed of 4 mm/second (45 rpm) along an ellipse of 2 mm in long axis and 1 mm of short axis (with moving the sample container). For the light measurement, a measurement by photon counting with BIN TIME of 10 μseconds for 20 seconds was continuously performed in 30 times (Namely, the light measurement was continuously performed for 600 seconds.). Also, in the case without only moving of the position of the sample container, the measurement was conducted under the same conditions except the moving of the sample solution (without moving the sample container).

In the data processing after the optical measurement, there were counted signals indicating light from a light-emitting particle detected in the time series photon count data acquired with the sample solutions under the respective conditions in accordance with the procedures described in the above-mentioned "(3)(i) Detection of A Signal Corresponding to a Light-emitting particle". In the smoothing of the data by the moving average method in step 110, 9 data points were averaged at once and the moving average treatment was repeated 5 times. Further, in the fitting of step 140, the fitting of a Gauss function to time series data was carried out by the least square method to determine the peak intensity, peak width (full width at half maximum) and correlation coefficient (of the Gauss function). Furthermore, in the judgment process in step 150, only a pulse signal satisfying the following conditions was judged as a signal corresponding to a light-emitting particle:

20 μseconds<pulse width<400 μseconds

Peak intensity>1.0*[pc*/10 μsec.]

Correlation coefficient>0.95,  (A)

while a pulse signal which did not satisfy the above-mentioned conditions was disregarded as a noise, and the number of the signals judged as signals corresponding to the light-emitting particles was counted as the "number of pulses." In this regard, the threshold value of the above-mentioned peak intensity was a magnitude to the degree in which noise of photodetector APD did not be erroneously detected as a signal of a light-emitting particle.

FIG. 6B shows the average values (bar graph) and the CV values (error bar) of the detected numbers of the light-emitting particles measured for the sample solutions prepared with various concentrations of the target nucleic acid according to the above-mentioned procedures. The values in the drawing are the average values and CV values computed from the detected numbers in 30 measurements where a measurement for 20 seconds is 1 time. Referring to the drawing, in the sample solutions of the respective concentrations, there was seen no large difference in the average values of the detected numbers between the case with moving the sample container and the case without moving the sample container, but, as for the CV values, it was 5 to 19% in the case without moving the sample container while it was 2 to 3% in the case with moving the sample container, where the scattering of the results was significantly reduced. Furthermore, considering that the sensitivity of the detected number to the concentration is 1SD, the lower limit of discriminable concentration was 50 pM in the case without moving the sample container while it was 500 fM in the case with moving the sample container, and accordingly, an improvement of 100 times was obtained. Namely, according to the above-mentioned results, it has been confirmed that the reduction of the scattering and the improvement of accuracy in result values of detected numbers of light-emitting particles can be achieved according the present invention.

Moreover, FIG. 6C shows variations of the average value for the light-emitting particles when the measurement for 20 seconds was continuously repeated 30 times with the sample solution of the target nucleic acid concentration of 50 pM. In this connection, the ordinate axis indicates the ratios of the detected numbers in the respective times to the number of particles detected in the first time (in the first 20 seconds). As seen clearly in the drawing, the detected number of the light-emitting particles per one time (per for 20 seconds) hardly changed when the moving of the sample container was performed during the measurements of 30 times, while it undulated and reduced to about 55% when the moving of the sample container was not performed. In the light-emitting particle in the present embodiment, as noted above, the molecular beacon emits fluorescence when it binds with a target nucleic acid molecule so that its existence becomes detectable, and therefore, it is considered that the undulation and reduction of the detected number in the same sample solution were caused by the bleaching of the fluorescent dyes. And, because the bleaching of fluorescent dyes is progressed in accordance with the dose of excitation light to the dyes, the undulation and reduction of the detected number owing to the bleaching of the fluorescent dyes when the moving of the sample container was not performed suggests that a light-emitting particle did not deviate from the scanning track of the light detection region during the light detection region circulating along the scanning track one time or more, and thereby, the light-emitting particle was irradiated repetitively with the excitation light. On the other hand, it is considered that, in the case with moving the sample container, since a different light-emitting particle always sequentially entered into the light detection region, the bleaching of the fluorescent dyes hardly occurred.

Thus, as understood from the results of the above-mentioned embodiment, it has been confirmed that, by moving the position of a sample solution while a light detection region is made circulate along a scanning track in accordance with the teaching of the present invention, the repetitive irradiation of the same particle with excitation light can be avoided and the possibility of misidentifying the same particles as different particles can be reduced, and also, the reduction of the scattering and the improvement of accuracy of the detected number of particles can be achieved by enabling the scanning of a broader area.

The invention claimed is:

1. An optical analysis device which detects light from a light-emitting particle dispersed and moving at random in a sample solution using an optical system of a confocal microscope or a multiphoton microscope, comprising:
   a light detection region mover which moves a position of a light detection region of the optical system in a flat plane in the sample solution;
   a light detector which detects light from the light detection region; and
   a signal processor which generates time series light intensity data of the light from the light detection region detected with the light detector with moving the position of the light detection region in the sample solution and detects a signal indicating light from each light-emitting particle individually in the time series light intensity data;
   wherein the light detection region mover moves the position of the light detection region along a second route whose position moves along a first route,
   wherein the first and the second routes are cyclic routes, and a moving cycle time of the position of the light detection region along the second route is shorter than a moving cycle time of the position of the second route along the first route.

2. The device of claim 1, wherein a moving cycle time $\tau 1$ of the position of the light detection region, a moving speed $v2$ of the position of the second route and a diameter $d$ of the light detection region satisfy $$v2\tau 1 > d.$$

3. The device of claim 1, wherein the position of the light detection region is moved along the second route by changing the optical path of the optical system; and the position of the second route is moved along the first route in the sample solution by moving the position of the sample solution.

4. The device of claim 1, wherein the second route is circular or elliptical, and the first route is circular, elliptical or linear.

5. The device of claim 1, wherein the light detection region mover moves the position of the light detection region at a speed quicker than a diffusion moving velocity of the light-emitting particle.

6. The device of claim 1, wherein the signal processor counts a number of individually detected signals indicating light from the light-emitting particles to count a number of the light-emitting particles detected during the moving of the position of the light detection region.

7. The device of claim 1, wherein the signal processor detects that one light-emitting particle has entered into the light detection region when a signal indicating light having a larger intensity than a predetermined threshold value is detected.

8. The device of claim 1, wherein the signal processor smoothes the time series light intensity data; and detects a bell-shaped pulse form signal having an intensity exceeding beyond a predetermined threshold value as a signal indicating light from a single light-emitting particle in the smoothed time series light intensity data.

9. The device of claim 1, wherein the signal processor determines a number density or a concentration of the light-emitting particle in the sample solution based on a number of the detected light-emitting particles.

10. An optical analysis method of detecting light from a light-emitting particle dispersed and moving at random in a sample solution using an optical system of a confocal microscope or a multiphoton microscope, comprising steps of:
    (a) moving a position of a light detection region of the optical system in a flat plane in the sample solution;
    (b) detecting light from the light detection region and generating time series light intensity data during the moving of the position of the light detection region; and
    (c) detecting individually a signal indicating light from each light-emitting particle using the time series light intensity data;
    wherein in the step (a), the light detection region is moved along a second route whose position moves along a first route,
    wherein the first and the second routes are cyclic routes, and a moving cycle time of the position of the light detection region along the second route is shorter than a moving cycle time of the position of the second route along the first route.

11. The method of claim 10, wherein a moving cycle time $\tau 1$ of the position of the light detection region, a moving speed $v2$ of the position of the second route and a diameter $d$ of the light detection region satisfy $$v2\tau 1 > d.$$

12. The method of claim 10, wherein the position of the light detection region is moved along the second route by changing the optical path of the optical system; and the position of the second route is moved along the first route in the sample solution by moving the position of the sample solution.

13. The method of claim 10, wherein the second route is circular or elliptical, and the first route is circular, elliptical or linear.

14. The method of claim 10, wherein, in the step (a), the position of the light detection region is moved at a speed quicker than a diffusion moving velocity of the light-emitting particle.

15. The method of claim 10, further comprising a step of (d) counting a number of individually detected signals indicating light from the light-emitting particles to count a number of the light-emitting particles detected during the moving of the position of the light detection region.

16. The method of claim 10, wherein, in the step (c), it is detected that one light-emitting particle has entered into the light detection region when a signal indicating light having a larger intensity than a predetermined threshold value is detected.

17. The method of claim 10, wherein, in the step (c), the time series light intensity data is smoothed; and a bell-shaped pulse form signal having an intensity exceeding beyond a predetermined threshold value is detected as a signal indicating light from a single light-emitting particle in the smoothed time series light intensity data.

18. The method of claim 10, further comprising a step of (e) determining a number density or a concentration of the light-emitting particle in the sample solution based on a number of the detected light-emitting particles.

19. A computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising:

moving a position of a light detection region of the optical system in a flat plane in the sample solution along a second route whose position moves along a first route in a flat plane in the sample solution;

detecting light from the light detection region and generating time series light intensity data during the moving of the position of the light detection region; and detecting individually a signal indicating light from each light-emitting particle using the time series light intensity data, wherein the first and the second routes are cyclic routes, and a moving cycle time of the position of the light detection region along the second route is shorter than a moving cycle time of the position of the second route along the first route.

20. The computer readable storage device of claim 19, wherein a moving cycle time $\tau 1$ of the position of the light detection region, a moving speed v2 of the position of the second route and a diameter d of the light detection region satisfy $$v2 \cdot \tau 1 > d.$$

21. The computer readable storage device of claim 19, wherein the position of the light detection region is moved along the second route by changing the optical path of the optical system; and the position of the second route is moved along the first route in the sample solution by moving the position of the sample solution.

22. The computer readable storage device of claim 19, wherein the second route is circular or elliptical, and the first route is circular, elliptical or linear.

23. The computer readable storage device of claim 19, wherein, in the step of moving the position of the light detection region, the position of the light detection region is moved at a speed quicker than a diffusion moving velocity of the light-emitting particle.

24. The computer readable storage device of claim 19, said programmed instructions causing a computer to further perform a step of counting a number of individually detected signals indicating light from the light-emitting particles to count a number of the light-emitting particles detected during the moving of the position of the light detection region.

25. The computer readable storage device of claim 19, wherein, in the step of detecting the signal, it is detected that one light-emitting particle has entered into the light detection region when a signal indicating light having a larger intensity than a predetermined threshold value is detected.

26. The computer readable storage device of claim 19, wherein, in the step of detecting the signal, the time series light intensity data is smoothed; and a bell-shaped pulse form signal having an intensity exceeding beyond a predetermined threshold value is detected as a signal indicating light from a single light-emitting particle in the smoothed time series light intensity data.

27. The computer readable storage device of claim 19, said programmed instructions causing a computer to further perform a step of determining a number density or a concentration of the light-emitting particle in the sample solution based on a number of the detected light-emitting particles.

* * * * *